US00PP34094P2

(12) United States Plant Patent
Mellema

(10) Patent No.: US PP34,094 P2
(45) Date of Patent: Apr. 5, 2022

(54) ***ALLIUM* PLANT NAMED 'IFALLS'**

(50) Latin Name: ***Allium senescens* subsp. *montanum***
Varietal Denomination: IFALLS

(71) Applicant: INNOFLORA PLANT BREEDING B.V., Heerhugowaard (NL)

(72) Inventor: Wietse Mellema, Creil (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/459,934

(22) Filed: Aug. 27, 2021

(51) Int. Cl.
*A01H 5/02* (2018.01)
*A01H 6/04* (2018.01)

(52) U.S. Cl.
USPC ..... Plt./263.1
CPC ..... *A01H 6/045* (2018.05)

(58) Field of Classification Search
USPC ..... Plt./263.1
CPC ..... A01H 6/045; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Allium* plant named 'IFALLS', characterized by its relatively compact and upright plant habit with outward flowering stems; moderately vigorous growth habit and moderately rapid growth rate; ensiform medium green-colored leaves; early and freely flowering habit; numerous light purple-colored flowers arranged on dense inflorescences; long flowering period; and good garden performance.

2 Drawing Sheets

Botanical designation: *Allium senescens* subsp. *montanum.*

Figure 1:
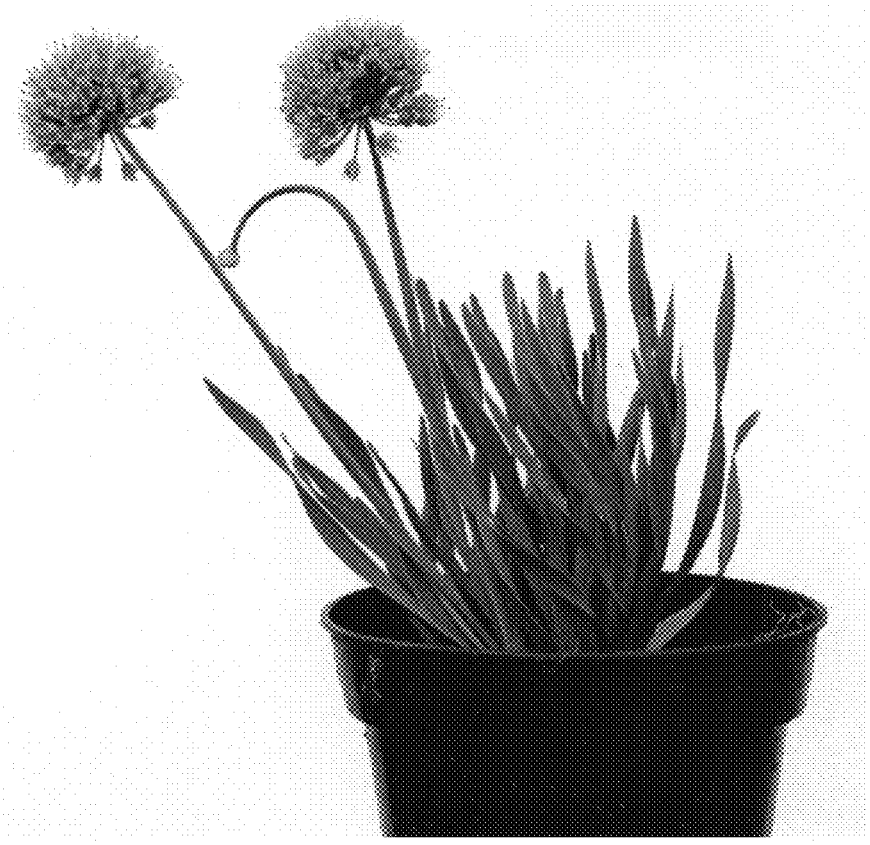

Cultivar denomination: 'IFALLS'.

PLANT BREEDER'S RIGHTS APPLICATION INFORMATION

An European Community Plant Breeder's Rights application for the instant plant was filed by the Applicant/Assignee, Innoflora Plant Breeding B.V. of Heerhugowaard, The Netherlands on Aug. 31, 2020, application number 2020/2059. Foreign priority is not claimed to this application.

BACKGROUND OF THE INVENTION

The present invention relates to a new and distinct cultivar of *Allium* plant, botanically known as *Allium senescens* subsp. *montanum* and hereinafter referred to by the name 'IFALLS'.

The new *Allium* plant is a product of a planned breeding program conducted by the Inventor in Heerhugowaard, The Netherlands. The objective of the breeding program is to create new compact and freely-flowering *Allium* plants with attractive flowers and good container and garden performance.

The new *Allium* plant originated from an open-pollination in May, 2007 of an unnamed selection of *Allium senescens* subsp. *montanum,* not patented, as the female, or seed, parent with an unknown selection of *Allium senescens* subsp. *montanum* as the male, or pollen, parent. The new *Allium* plant was discovered and selected by the Inventor as a single flowering plant from within the progeny of the stated open-pollination grown in a controlled greenhouse environment in Heerhugowaard, The Netherlands in 2010.

Asexual reproduction of the new *Allium* plant by divisions in a controlled environment in Heerhugowaard, The Netherlands since 2011 has shown that the unique features of this new *Allium* plant are stable and reproduced true to type in successive generations.

SUMMARY OF THE INVENTION

Plants of the new *Allium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFALLS'. These characteristics in combination distinguish 'IFALLS' as a new and distinct *Allium* plant:

1. Relatively compact and upright plant habit with outward flowering stems.
2. Moderately vigorous growth habit and moderately rapid growth rate.
3. Ensiform medium green-colored leaves.
4. Early and freely flowering habit.
5. Numerous light purple-colored flowers arranged on dense inflorescences.
6. Long flowering period.
7. Good garden performance.

Plants of the new *Allium* differ primarily from plants of the female parent selection in the following characteristics:

1. Plants of the new *Allium* are more compact than plants of the female parent selection.
2. Plants of the new *Allium* are more freely flowering than plants of the female parent selection.

Plants of the new *Allium* can be compared to plants of *Allium hybrida* 'Milennium', not patented. Plants of the new *Allium* differ primarily from plants of 'Milennium' in the following characteristics:

1. Plants of the new *Allium* are more compact than plants of 'Millennium'.
2. Plants of the new *Allium* are less vigorous than plants of 'Millennium'.

BRIEF DESCRIPTION OF THE PHOTOGRAPHS

The accompanying colored photographs illustrate the overall appearance of the new *Allium* plant showing the colors as true as it is reasonably possible to obtain in colored reproductions of this type. Colors in the photographs may differ slightly from the color values cited in the detailed botanical description which accurately describe the colors of the new *Allium* plant.

The photograph on the first sheet (FIG. 1) is a side perspective view of typical flowering plant of 'IFALLS' grown in a container.

Figure 2:
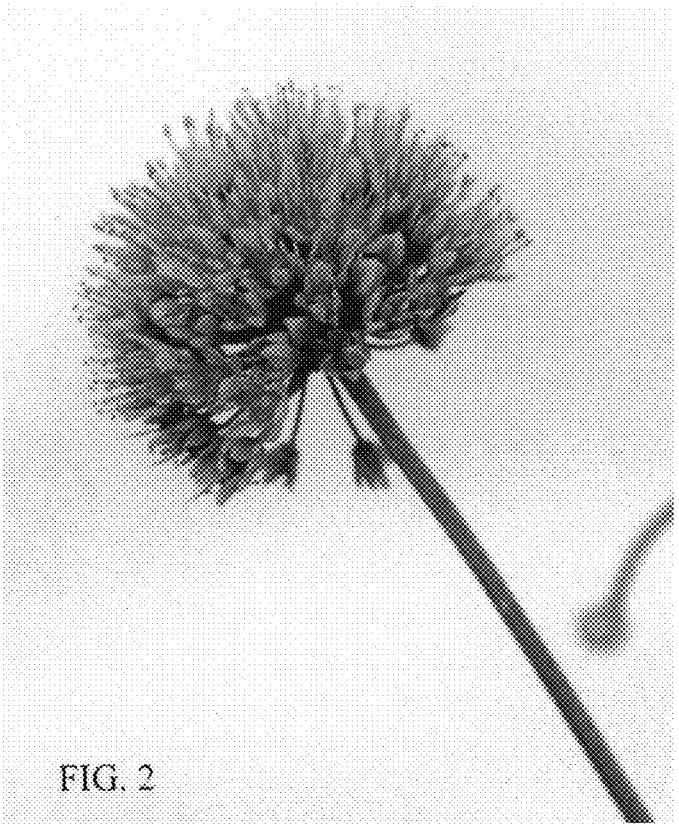

The photograph at the top of the second sheet (FIG. 2) is a close-up view of a typical inflorescence of 'IFALLS'.

Figure 3:
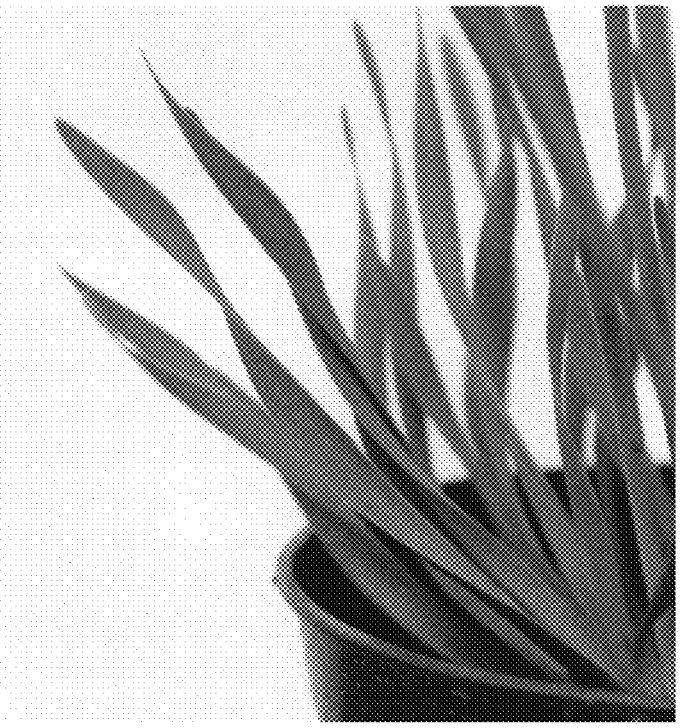

The photograph at the bottom of the second sheet (FIG. 3) is a close-up view of typical leaves of 'IFALLS'.

DETAILED BOTANICAL DESCRIPTION

The aforementioned photographs and following observations, measurements and values describe plants grown during the summer in 13-cm containers in an outdoor nursery in Heerhugowaard, The Netherlands and under cultural practices typical of commercial *Allium* production. During the production of the plants, day temperatures ranged from 16° C. to 40° C. and night temperatures ranged from 8° C. to 24° C. Plants were twelve months old when the photographs and description were taken. In the following description, color references are made to The Royal Horticultural Society Colour Chart, 2015 Edition, except where general terms of ordinary dictionary significance are used.

Botanical classification: *Allium tuberosum* 'IFALL'.

Parentage:

*Female, or seed, parent.*—Unnamed selection of *Allium senescens* subsp. *montanum*, not patented.

*Male, or pollen, parent.*—Unknown selection of *Allium senescens* subsp. *montanum*, not patented.

Propagation:

*Type.*—By divisions.

*Time to produce a rooted young plant, summer.*—About two months at temperatures about 18° C.

*Root description.*—Thick; fleshy; typically white in color, actual color of the roots is dependent on substrate composition, water quality, fertilizer type and formulation, substrate temperature and physiological age of roots.

*Rooting habit.*—Moderately freely branching; sparse.

*Bulbs.*—To date, bulb development has not been observed on plants of the new *Allium*.

Plant description:

*Plant and growth habit.*—Herbaceous perennial typically grown as a garden plant; relatively compact, upright plant habit, overall plant shape, broadly obovate; moderately vigorous growth habit and moderate growth rate; globular basal rosette of leaves with upright flowering stems.

*Plant height, soil level to top of foliar plane.*—About 16.8 cm.

*Plant height, soil level to top of floral plane.*—About 22.8 cm.

*Plant width* (*spread*).—About 27 cm.

Leaf description:

*Arrangement.*—Leaves are arranged in basal rosettes with about six to eleven leaves per rosette; leaves sheathing and sessile.

*Length.*—About 18.4 cm.

*Width.*—About 7 mm.

*Shape.*—Ensiform; blade is mostly flat and twisting axillary.

*Apex.*—Bluntly acute.

*Base.*—Sheathing.

*Margin.*—Entire, not undulate.

*Texture and luster, upper surface.*—Smooth, glabrous; glaucous; matte to slightly glossy.

*Texture and luster, lower surface.*—Smooth, glabrous; glaucous; slightly glossy.

*Venation pattern.*—Parallel.

*Color.*—Developing leaves, upper and lower surfaces: Close to 138A to 138B. Fully developed leaves, upper surface: Close to 137A; venation, close to 137A; thin waxy layer, close to 191C. Fully developed leaves, lower surface: Close to NN137B to NN137C; venation, close to NN137B to NN137C; thin waxy layer, close to 191C.

*Leaf sheaths.*—Length: About 4 cm. Diameter: About 1.8 cm. Texture and luster, upper and lower surfaces: Smooth, glabrous; slightly glossy. Color, upper and lower surfaces: Close to NN155D.

Flower description:

*Flower type, arrangement and habit.*—Single rotate flowers arranged on dense umbels; umbels globular in shape; freely flowering habit with about 90 flowers developing per inflorescence and about 180 flowers per plant; flowers face upright to outwardly to downward depending on position on the umbel.

*Natural flowering season.*—Plants flower from July into August in The Netherlands; plants begin flowering about six months after planting rooted young plants.

*Flower longevity on the plant.*—Individual flowers last about two weeks on the plant; flowers persistent.

*Fragrance.*—Faint; sweet and pleasant, onion-like.

*Flower buds.*—Length: About 5 mm. Diameter: About 4 mm. Shape: Obovate. Texture and luster: Smooth, glabrous; slightly glossy. Color: Close to 75A.

*Inflorescence height.*—About 5 cm.

*Inflorescence diameter.*—About 5.5 cm.

*Flower diameter.*—About 1 cm by 1 cm.

*Flower depth.*—About 1 cm.

*Tepals.*—Quantity and arrangement: Six arranged in two whorls. Upper whorl of tepals: Length: About 6 mm. Width: About 3 mm. Shape: Ovate, concave. Apex: Bluntly acute. Base: Broadly cuneate. Margin: Entire, not undulate. Texture and luster, upper surface: Smooth, glabrous; matte. Texture and luster, lower surface: Smooth, glabrous; slightly glossy. Color: When opening, upper and lower surfaces: Close to 75A; central band, close to N75B. Fully opened, upper and lower surfaces: Close to 76A; central band, close to N75B; venation, close to N75A; color becoming closer to 76A with subsequent development. Lower whorl of tepals: Length: About 5 mm. Width: About 2 mm. Shape: Ovate, concave. Apex: Bluntly acute. Base: Broadly cuneate. Margin: Entire, not undulate. Texture and luster, upper surface: Smooth, glabrous; matte. Texture and luster, lower surface: Smooth, glabrous; slightly glossy. Color: When opening, upper and lower surfaces: Close to 75A; central band, close to N75B. Fully opened, upper and lower surfaces: Close to 76A; central band, close to N75B; venation, close to N75A; color becoming closer to 76A with subsequent development.

*Scapes.*—Length: About 23.7 cm. Diameter: About 4 mm. Aspect: Outward, about 32.5° from vertical. Strength: Strong. Texture and luster: Smooth, glabrous; glaucous. Color: Close to NN137A; waxy layer, close to 194C.

*Pedicels.*—Length: About 1.8 cm. Diameter: About 0.8 mm. Aspect: Erect to horizontal to downward depending on position on umbel. Strength: Strong. Texture and luster: Smooth, glabrous; slightly glossy. Color: Close to 138B.

*Inflorescence bracts.*—Arrangement: Subtending the tepals and tri-parted. Length: About 8 mm. Width: About 5 mm. Texture: Papery. Color: Close to 161B.

*Reproductive organs.*—Stamens: Quantity per flower: Six. Filament length: About 6.5 mm. Filament color: Close to 76A. Anther shape: Basifixed, oblong. Anther size: About 0.8 mm by 1.5 mm. Anther color: Close to 164C. Pollen amount: Scarce. Pollen color: Close to 157A. Pistils: Quantity per flower: One. Pistil length: About 3 mm. Style length: About 2.5 mm. Style color: Close to N80D. Stigma size: About 0.3 mm by 0.5 mm. Stigma shape: Pointed. Stigma color: Close to N187D. Ovary color: Close to N80D.

*Seeds and fruits.*—To date, seed and fruit production have not been observed on plants of the new *Allium.*

Pathogen & pest resistance: To date, plants of the new *Allium* have not been observed to be resistant to pathogens and pests common to *Allium* plants.

Garden performance: Plants of the new *Allium* have exhibited good tolerance to rain, wind and temperatures ranging from about −23° C. to about 40° C. and to be suitable for USDA Hardiness Zones 5 to 10.

It is claimed:

1. A new and distinct *Allium* plant named 'IFALLS' as illustrated and described.

* * * * *